United States Patent
Belson et al.

(10) Patent No.: US 12,102,880 B2
(45) Date of Patent: *Oct. 1, 2024

(54) EXERCISE MACHINE SUGGESTED WEIGHTS

(71) Applicant: Tonal Systems, Inc., San Francisco, CA (US)

(72) Inventors: Brandt Belson, San Francisco, CA (US); Meeran Ismail, San Francisco, CA (US); Sungsu Lim, Toronto (CA); Pavel Katkov, Samara (RU); Egor Ponomarev, Samara (RU); Ekaterina Pugovkina, Samara (RU)

(73) Assignee: Tonal Systems, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/094,014

(22) Filed: Jan. 6, 2023

(65) Prior Publication Data

US 2023/0218950 A1 Jul. 13, 2023

Related U.S. Application Data

(63) Continuation of application No. 17/700,462, filed on Mar. 21, 2022, now Pat. No. 11,596,837.

(60) Provisional application No. 63/298,395, filed on Jan. 11, 2022.

(51) Int. Cl.
| | |
|---|---|
| *A63B 24/00* | (2006.01) |
| *A63B 21/005* | (2006.01) |
| *A63B 71/00* | (2006.01) |
| *G16H 20/30* | (2018.01) |

(52) U.S. Cl.
CPC ...... *A63B 24/0087* (2013.01); *A63B 21/0058* (2013.01); *G16H 20/30* (2018.01); *A63B 2024/0078* (2013.01); *A63B 2024/0093* (2013.01); *A63B 2071/0072* (2013.01)

(58) Field of Classification Search
CPC ............ A63B 24/0087; A63B 21/0058; A63B 2024/0078; A63B 2024/0093; A63B 2071/0072; A63B 21/4035; A63B 2220/10; A63B 2220/40; A63B 2220/51; A63B 2220/805; A63B 24/0075; A63B 2220/54; G16H 20/30; G16H 40/63
See application file for complete search history.

(56) References Cited

U.S. PATENT DOCUMENTS

| | | |
|---|---|---|
| 4,828,257 A | 5/1989 | Dyer |
| 4,934,694 A | 6/1990 | McIntosh |
| 5,785,630 A | 7/1998 | Bobick |
| 5,890,995 A | 4/1999 | Bobick |
| 5,993,356 A | 11/1999 | Houston |
| 6,921,351 B1 | 7/2005 | Hickman |
| 8,388,499 B1 | 3/2013 | Rindfleisch |
| 8,900,097 B1 | 12/2014 | Griggs |

(Continued)

*Primary Examiner* — Sundhara M Ganesan
(74) *Attorney, Agent, or Firm* — Van Pelt, Yi & James LLP

(57) ABSTRACT

An exercise machine comprises an actuator, a motor coupled to the actuator, and a motor controller coupled to the motor. The motor controller is configured to receive an indication of a characteristic of a workout on the actuator, wherein the workout comprises a next exercise movement, determine a suggested weight for the next exercise movement, based at least in part on a physiological analysis of the workout characteristic, and control torque of the motor for the next exercise movement, based at least in part on the suggested weight.

21 Claims, 8 Drawing Sheets

(56) References Cited

U.S. PATENT DOCUMENTS

| | | |
|---|---|---|
| 8,900,099 B1 | 12/2014 | Boyette |
| 9,707,435 B1 | 7/2017 | Ferlito |
| 11,130,022 B1 | 9/2021 | Loduca |
| 2004/0209738 A1 | 10/2004 | Crawford |
| 2005/0164837 A1 | 7/2005 | Anderson |
| 2010/0069202 A1 | 3/2010 | Olsen |
| 2011/0082006 A1 | 4/2011 | Ishii |
| 2011/0294624 A1 | 12/2011 | Burnfield |
| 2012/0053014 A1 | 3/2012 | Zhu |
| 2012/0231929 A1 | 9/2012 | Hsieh |
| 2012/0329607 A1 | 12/2012 | Wang |
| 2013/0005535 A1 | 1/2013 | Duchovne |
| 2013/0065730 A1 | 3/2013 | Camerota |
| 2013/0267384 A1 | 10/2013 | Eldridge |
| 2013/0274063 A1 | 10/2013 | Tyger |
| 2013/0310230 A1 | 11/2013 | Norris |
| 2014/0038777 A1 | 2/2014 | Bird |
| 2014/0135174 A1 | 5/2014 | Potash |
| 2014/0194250 A1 | 7/2014 | Reich |
| 2014/0213414 A1 | 7/2014 | Balandis |
| 2014/0228174 A1 | 8/2014 | Olsen |
| 2014/0276273 A1 | 9/2014 | Leismer |
| 2014/0287876 A1 | 9/2014 | Etter |
| 2014/0296040 A1 | 10/2014 | Mobley |
| 2014/0342878 A1 | 11/2014 | Hashish |
| 2015/0005911 A1 | 1/2015 | Lake, II |
| 2015/0031505 A1 | 1/2015 | Hsieh |
| 2015/0072835 A1 | 3/2015 | Kunstmann |
| 2015/0141200 A1 | 5/2015 | Murray |
| 2015/0335951 A1 | 11/2015 | Eder |
| 2016/0059077 A1 | 3/2016 | Paul |
| 2016/0151675 A1 | 6/2016 | Chazalon |
| 2016/0184628 A1 | 6/2016 | Quinn |
| 2017/0080287 A1 | 3/2017 | Jaquish |
| 2017/0095695 A1 | 4/2017 | Mangusson |
| 2017/0173396 A1 | 6/2017 | Lu |
| 2017/0209327 A1 | 7/2017 | Hou |
| 2017/0209737 A1 | 7/2017 | Tadi |
| 2017/0282015 A1 | 10/2017 | Wicks |
| 2017/0361165 A1 | 12/2017 | Miller |
| 2018/0214729 A1 | 8/2018 | Rubin |
| 2018/0243599 A1 | 8/2018 | Lacey |
| 2018/0326242 A1 | 11/2018 | Jaquish |
| 2019/0099633 A1 | 4/2019 | Orady |
| 2019/0099637 A1 | 4/2019 | Valente |
| 2019/0099652 A1 | 4/2019 | Orady |
| 2019/0160324 A1 | 5/2019 | Leopoldo Da Camara Filho |
| 2020/0047055 A1 | 2/2020 | Ward |
| 2020/0054914 A1 | 2/2020 | Lafrance |
| 2020/0070005 A1 | 3/2020 | Lin |
| 2020/0070032 A1 | 3/2020 | Orady |
| 2020/0298062 A1 | 9/2020 | Gilstrom |
| 2021/0220703 A1 | 7/2021 | Lee |
| 2021/0220704 A1 | 7/2021 | Claudio |
| 2021/0260444 A1 | 8/2021 | Huang |
| 2021/0322830 A1 | 10/2021 | Blaszczyk |
| 2021/0387038 A1 | 12/2021 | Premachandra |
| 2021/0394011 A1 | 12/2021 | Neuhaus |
| 2021/0394023 A1 | 12/2021 | Belson |
| 2021/0402259 A1 | 12/2021 | Belson |
| 2022/0047921 A1 | 2/2022 | Bissonnette |
| 2022/0072367 A1 | 3/2022 | Wang |
| 2022/0105378 A1 | 4/2022 | Chiavegato |
| 2022/0143466 A1 | 5/2022 | Zoffoli |

EXERCISE MACHINE SUGGESTED WEIGHTS

CROSS REFERENCE TO OTHER APPLICATIONS

This application is a continuation of U.S. patent application Ser. No. 17/700,462, entitled EXERCISE MACHINE SUGGESTED WEIGHTS filed Mar. 21, 2022 which is incorporated herein by reference for all purposes, which claims priority to U.S. Provisional Patent Application No. 63/298,395 entitled SUGGESTED WEIGHTS filed Jan. 11, 2022 which is incorporated herein by reference for all purposes.

BACKGROUND OF THE INVENTION

Strength training may eventually be demotivational for a user. One aspect of this is a feeling of a lack of progress over time. When maintaining a strength training regimen, users are often at a loss as to what weight levels to choose for a given movement, which may contribute to this feeling of a lack of progress if the chosen weight levels are inappropriate.

BRIEF DESCRIPTION OF THE DRAWINGS

Various embodiments of the invention are disclosed in the following detailed description and the accompanying drawings.

DETAILED DESCRIPTION

Figure 1:
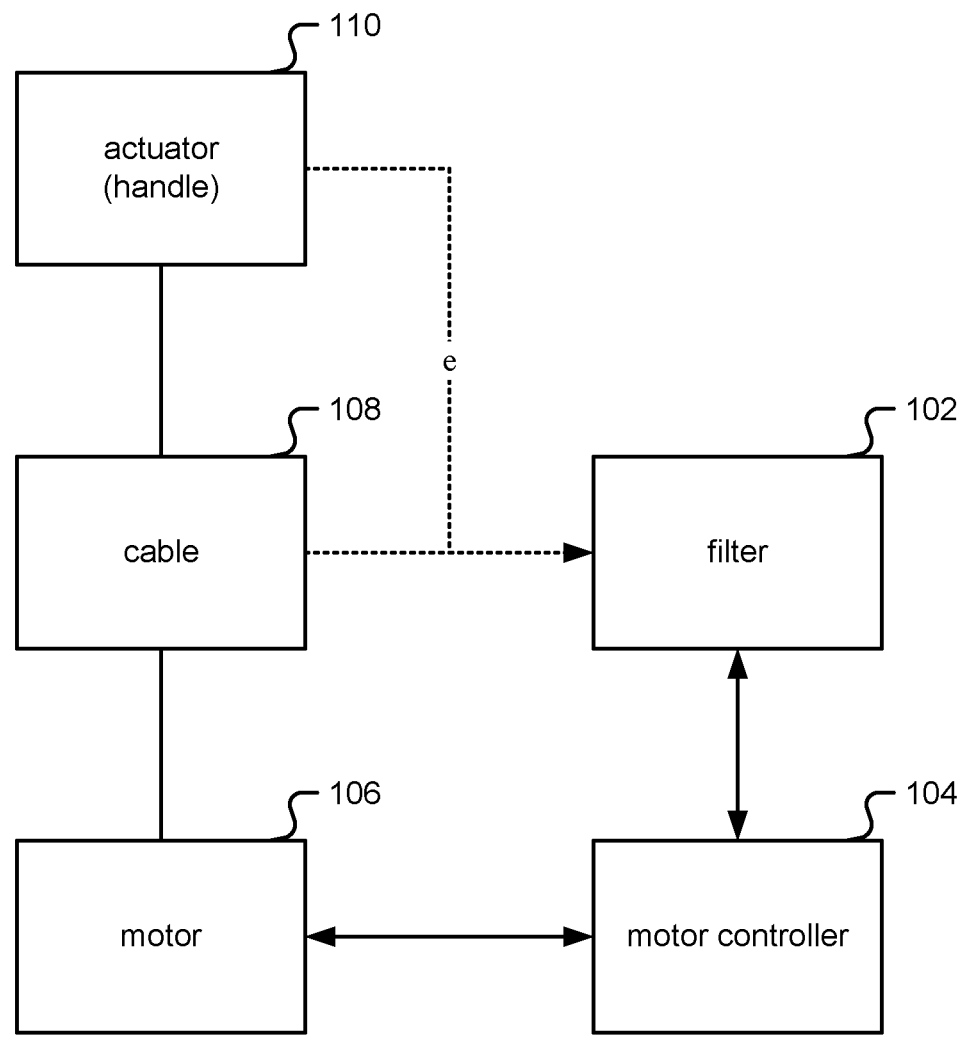
FIG. 1 is a block diagram illustrating an embodiment of an exercise machine capable of digital strength training.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Suggesting appropriate weights and/or resistance for a user's exercise set using an exercise machine is disclosed. In one embodiment, the exercise machine comprises a motor wherein the torque of the motor is associated with resistance for the exercise machine, for example emulating a "digital weight" for the user of the exercise machine.

The disclosed techniques may thus be used with any machine where motor torque is associated with resistance, for example using a digital strength training technique as described in U.S. Pat. No. 10,661,112 entitled DIGITAL STRENGTH TRAINING filed Jul. 20, 2017, and U.S. Pat. No. 10,335,626 entitled EXERCISE MACHINE WITH PANCAKE MOTOR filed Jul. 2, 2019, which are incorporated herein by reference for all purposes. Any person of ordinary skill in the art understands that the strength determination techniques may be used without limitation with other machines capable of associating motor torque with resistance, and the digital strength trainer is given merely as an example embodiment.

Using a characteristic of a user's workout to determine a suggested weight for a next exercise movement is disclosed.

Determining suggested weights for an upcoming repetition (as referred to herein as a "rep") and/or set of repetitions (as referred to herein as a "set") based at least in part on previous sets and/or reps is disclosed. An indication of workout intensity, for example weight percentage, associated with a previous set of an exercise movement is evaluated. In one embodiment, the indication of workout intensity associated with the previous set of the exercise movement is evaluated against a threshold. Based at least in part on the evaluation, performance information pertaining to the previous set of the exercise movement may be used to determine a suggested weight for an upcoming set of the exercise movement. Torque of the exercise machine motor may then be controlled based at least in part on the suggested weight.

Determining a suggested weight for duration-based sets is disclosed. After determining that a duration-based set of an exercise movement is to be performed, a repetition goal is determined based at least in part on one or more characteristics of the duration-based set of the exercise movement. In one embodiment, a suggested weight for the duration-based set of the exercise movement is determined based at least in part on the repetition goal. Torque of the exercise machine motor may then be controlled based at least in part on the suggested weight.

Determining a suggested weight based on relative muscle volume is disclosed. After identifying a plurality of muscle groups utilized across a plurality of exercise movements included in a workout, a corresponding relative muscle volume for each muscle group in the plurality of muscle groups may be determined. In one embodiment, a suggested weight for an exercise movement in the plurality of exercise movements included in the workout is determined based at least in part on a relative muscle volume determined for an associated muscle group. Torque of the exercise machine motor may then be controlled based at least in part on the suggested weight.

Before suggesting weights, an initial strength calibration may be used, for example using strength calibration as described in U.S. Pat. No. 10,874,905 entitled STRENGTH CALIBRATION filed Feb. 14, 2019, which is incorporated herein by reference for all purposes.

Strength Determination/Calibration. Strength determination and/or calibration of a user based on only a few specific movements is described. This strength determination may be used as a starting basis for a strength level for the user for hundreds of strength training movements, for getting a user started on a strength training machine, and/or for calibrating progress. The strength determination is based at least in part on an "isokinetic seed movement". An isokinetic seed movement as referred to herein is a movement wherein the user is allowed to move against a machine's resistance at a prescribed constant speed during a movement's concentric, or eccentric, phase, and the machine's resistance dynamically changes to match the user's applied force. The user's produced force at the prescribed speed is mapped to a predetermined force-velocity profile/plot ("FVP") to determine strength, for example an estimated one rep maximum ("1eRM") for the user for the muscle group associated with the isokinetic seed movement, wherein the 1eRM is an estimate of the one rep maximum, or how much weight a user could maximally exercise for a given movement for a single cycle, that is without further repetition. This 1eRM may be used to recommend starting weights for future non-isokinetic movements, for example regular strength training movements.

Traditionally, one method of calibrating a user's strength is to ask a user to perform one or more movements, and do so to the point of physical failure. However, this approach is manual, painful to users, and may even injure some users. An improvement of the described is the providing of an automated way of calibrating a user's strength level that additionally reduces a risk of injury for the user.

The described techniques may be used with any machine capable of these, or other, isokinetic seed movements. Any person of ordinary skill in the art understands that the strength determination techniques may be used without limitation with other machines capable of isokinetic seed movements, and the digital strength trainer is given merely as an example embodiment.

FIG. 1 is a block diagram illustrating an embodiment of an exercise machine capable of digital strength training. The exercise machine includes the following:

- a controller circuit (104), which may include a processor, inverter, pulse-width-modulator, and/or a Variable Frequency Drive (VFD);
- a motor (106), for example a three-phase brushless DC driven by the controller circuit;
- a spool with a cable (108) wrapped around the spool and coupled to the spool. On the other end of the cable an actuator/handle (110) is coupled in order for a user to grip and pull on. The spool is coupled to the motor (106) either directly or via a shaft/belt/chain/gear mechanism. Throughout this specification, a spool may be also referred to as a "hub";
- a filter (102), to digitally control the controller circuit (104) based on receiving information from the cable (108) and/or actuator (110);
- optionally (not shown in FIG. 1) a gearbox between the motor and spool. Gearboxes multiply torque and/or friction, divide speed, and/or split power to multiple spools. Without changing the fundamentals of digital strength training, a number of combinations of motor and gearbox may be used to achieve the same end result. A cable-pulley system may be used in place of a gearbox, and/or a dual motor may be used in place of a gearbox;
- one or more of the following sensors (not shown in FIG. 1): a position encoder; a sensor to measure position of the actuator (110). Examples of position encoders include a hall effect shaft encoder, grey-code encoder on the motor/spool/cable (108), an accelerometer in the actuator/handle (110), optical sensors, position measurement sensors/methods built directly into the motor (106), and/or optical encoders. In one embodiment, an optical encoder is used with an encoding pattern that uses phase to determine direction associated with the low resolution encoder. Other options that measure back-EMF (back electromagnetic force) from the motor (106) in order to calculate position also exist;
- a motor power sensor; a sensor to measure voltage and/or current being consumed by the motor (106);
- a user tension sensor; a torque/tension/strain sensor and/or gauge to measure how much tension/force is being applied to the actuator (110) by the user. In one embodiment, a tension sensor is built into the cable (108). Alternatively, a strain gauge is built into the motor mount holding the motor (106). As the user pulls on the actuator (110), this translates into strain on the motor mount which is measured using a strain gauge in a Wheatstone bridge configuration. In another embodiment, the cable (108) is guided through a pulley coupled to a load cell. In another embodiment, a belt coupling the motor (106) and cable spool or gearbox (108) is guided through a pulley coupled to a load cell. In another embodiment, the resistance generated by the motor (106) is characterized based on the voltage, current, or frequency input to the motor.

In one embodiment, a three-phase brushless DC motor (106) is used with the following:

- a controller circuit (104) combined with filter (102) comprising:
- a processor that runs software instructions;
- three pulse width modulators (PWMs), each with two channels, modulated at 20 kHz;
- six transistors in an H-Bridge configuration coupled to the three PWMs;
- optionally, two or three ADCs (Analog to Digital Converters) monitoring current on the H-Bridge; and/or
- optionally, two or three ADCs monitoring back-EMF voltage;
- the three-phase brushless DC motor (106), which may include a synchronous-type and/or asynchronous-type permanent magnet motor, such that:
- the motor (106) may be in an "out-runner configuration" as described below;
- the motor (106) may have a maximum torque output of at least 60 Nm and a maximum speed of at least 300 RPMs;
- optionally, with an encoder or other method to measure motor position;

a cable (108) wrapped around the body of the motor (106) such that entire motor (106) rotates, so the body of the motor is being used as a cable spool in one case. Thus, the motor (106) is directly coupled to a cable (108) spool. In one embodiment, the motor (106) is coupled to a cable spool via a shaft, gearbox, belt, and/or chain, allowing the diameter of the motor (106) and the diameter of the spool to be independent, as well as introducing a stage to add a set-up or step-down ratio if desired. Alternatively, the motor (106) is coupled to two spools with an apparatus in between to split or share the power between those two spools. Such an apparatus could include a differential gearbox, or a pulley configuration; and/or an actuator (110) such as a handle, a bar, a strap, or other accessory connected directly, indirectly, or via a connector such as a carabiner to the cable (108).

In some embodiments, the controller circuit (102, 1004) is programmed to drive the motor in a direction such that it draws the cable (108) towards the motor (106). The user pulls on the actuator (110) coupled to cable (108) against the direction of pull of the motor (106).

One purpose of this setup is to provide an experience to a user similar to using a traditional cable-based strength training machine, where the cable is attached to a weight stack being acted on by gravity. Rather than the user resisting the pull of gravity, they are instead resisting the pull of the motor (106).

Note that with a traditional cable-based strength training machine, a weight stack may be moving in two directions: away from the ground or towards the ground. When a user pulls with sufficient tension, the weight stack rises, and as that user reduces tension, gravity overpowers the user and the weight stack returns to the ground.

By contrast in a digital strength trainer, there is no actual weight stack. The notion of the weight stack is one modeled by the system. The physical embodiment is an actuator (110) coupled to a cable (108) coupled to a motor (106). A "weight moving" is instead translated into a motor rotating. As the circumference of the spool is known and how fast it is rotating is known, the linear motion of the cable may be calculated to provide an equivalency to the linear motion of a weight stack. Each rotation of the spool equals a linear motion of one circumference or $2\pi r$ for radius r. Likewise, torque of the motor (106) may be converted into linear force by multiplying it by radius r.

If the virtual/perceived "weight stack" is moving away from the ground, motor (106) rotates in one direction. If the "weight stack" is moving towards the ground, motor (106) rotates in the opposite direction. Note that the motor (106) is pulling towards the cable (108) onto the spool. If the cable (108) is unspooling, it is because a user has overpowered the motor (106). Thus, note a distinction between the direction the motor (106) is pulling, and the direction the motor (106) is actually turning.

If the controller circuit (102, 1004) is set to drive the motor (106) with, for example, a constant torque in the direction that spools the cable, corresponding to the same direction as a weight stack being pulled towards the ground, then this translates to a specific force/tension on the cable (108) and actuator (110). Calling this force "Target Tension", this force may be calculated as a function of torque multiplied by the radius of the spool that the cable (108) is wrapped around, accounting for any additional stages such as gear boxes or belts that may affect the relationship between cable tension and torque. If a user pulls on the actuator (110) with more force than the Target Tension, then that user overcomes the motor (106) and the cable (108) unspools moving towards that user, being the virtual equivalent of the weight stack rising. However, if that user applies less tension than the Target Tension, then the motor (106) overcomes the user and the cable (108) spools onto and moves towards the motor (106), being the virtual equivalent of the weight stack returning.

BLDC Motor. While many motors exist that run in thousands of revolutions per second, an application such as fitness equipment designed for strength training has different requirements and is by comparison a low speed, high torque type application suitable for a BLDC motor.

In one embodiment, a requirement of such a motor (106) is that a cable (108) wrapped around a spool of a given diameter, directly coupled to a motor (106), behaves like a 200 lbs weight stack, with the user pulling the cable at a maximum linear speed of 62 inches per second. A number of motor parameters may be calculated based on the diameter of the spool.

| | User Requirements | | | | | |
|---|---|---|---|---|---|---|
| Target Weight | 200 lbs | | | | | |
| Target Speed | 62 inches/sec = 1.5748 meters/sec | | | | | |

| | Requirements by Spool Size | | | | | |
|---|---|---|---|---|---|---|
| | Diameter (inches) | | | | | |
| | 3 | 5 | 6 | 7 | 8 | 9 |
| RPM | 394.7159 | 236.82954 | 197.35795 | 169.1639572 | 148.0184625 | 131.5719667 |
| Torque (Nm) | 67.79 | 112.9833333 | 135.58 | 158.1766667 | 180.7733333 | 203.37 |
| Circumference (inches) | 9.4245 | 15.7075 | 18.849 | 21.9905 | 25.132 | 28.2735 |

Thus, a motor with 67.79 Nm of force and a top speed of 395 RPM, coupled to a spool with a 3 inch diameter meets these requirements. 395 RPM is slower than most motors available, and 68 Nm is more torque than most motors on the market as well.

Hub motors are three-phase permanent magnet BLDC direct drive motors in an "out-runner" configuration: throughout this specification out-runner means that the permanent magnets are placed outside the stator rather than inside, as opposed to many motors which have a permanent magnet rotor placed on the inside of the stator as they are designed more for speed than for torque. Out-runners have the magnets on the outside, allowing for a larger magnet and pole count and are designed for torque over speed. Another way to describe an out-runner configuration is when the shaft is fixed and the body of the motor rotates.

Hub motors also tend to be "pancake style". As described herein, pancake motors are higher in diameter and lower in depth than most motors. Pancake style motors are advantageous for a wall mount, subfloor mount, and/or floor mount application where maintaining a low depth is desirable, such as a piece of fitness equipment to be mounted in a consumer's home or in an exercise facility/area. As described herein, a pancake motor is a motor that has a diameter higher than twice its depth. As described herein, a pancake motor is between 15 and 60 centimeters in diameter, for example 22 centimeters in diameter, with a depth between 6 and 15 centimeters, for example a depth of 6.7 centimeters.

Motors may also be "direct drive", meaning that the motor does not incorporate or require a gear box stage. Many motors are inherently high speed low torque but incorporate an internal gearbox to gear down the motor to a lower speed with higher torque and may be called gear motors. Direct drive motors may be explicitly called as such to indicate that they are not gear motors.

If a motor does not exactly meet the requirements illustrated in the table above, the ratio between speed and torque may be adjusted by using gears or belts to adjust. A motor coupled to a 9" sprocket, coupled via a belt to a spool coupled to a 4.5" sprocket doubles the speed and halves the torque of the motor. Alternately, a 2:1 gear ratio may be used to accomplish the same thing. Likewise, the diameter of the spool may be adjusted to accomplish the same.

Alternately, a motor with 100× the speed and 100th the torque may also be used with a 100:1 gearbox. As such a gearbox also multiplies the friction and/or motor inertia by 100×, torque control schemes become challenging to design for fitness equipment/strength training applications. Friction may then dominate what a user experiences. In other applications friction may be present, but is low enough that it is compensated for, but when it becomes dominant, it is difficult to control for. For these reasons, direct control of motor speed and/or motor position as with BLDC motors is more appropriate for fitness equipment/strength training systems.

Figure 2:
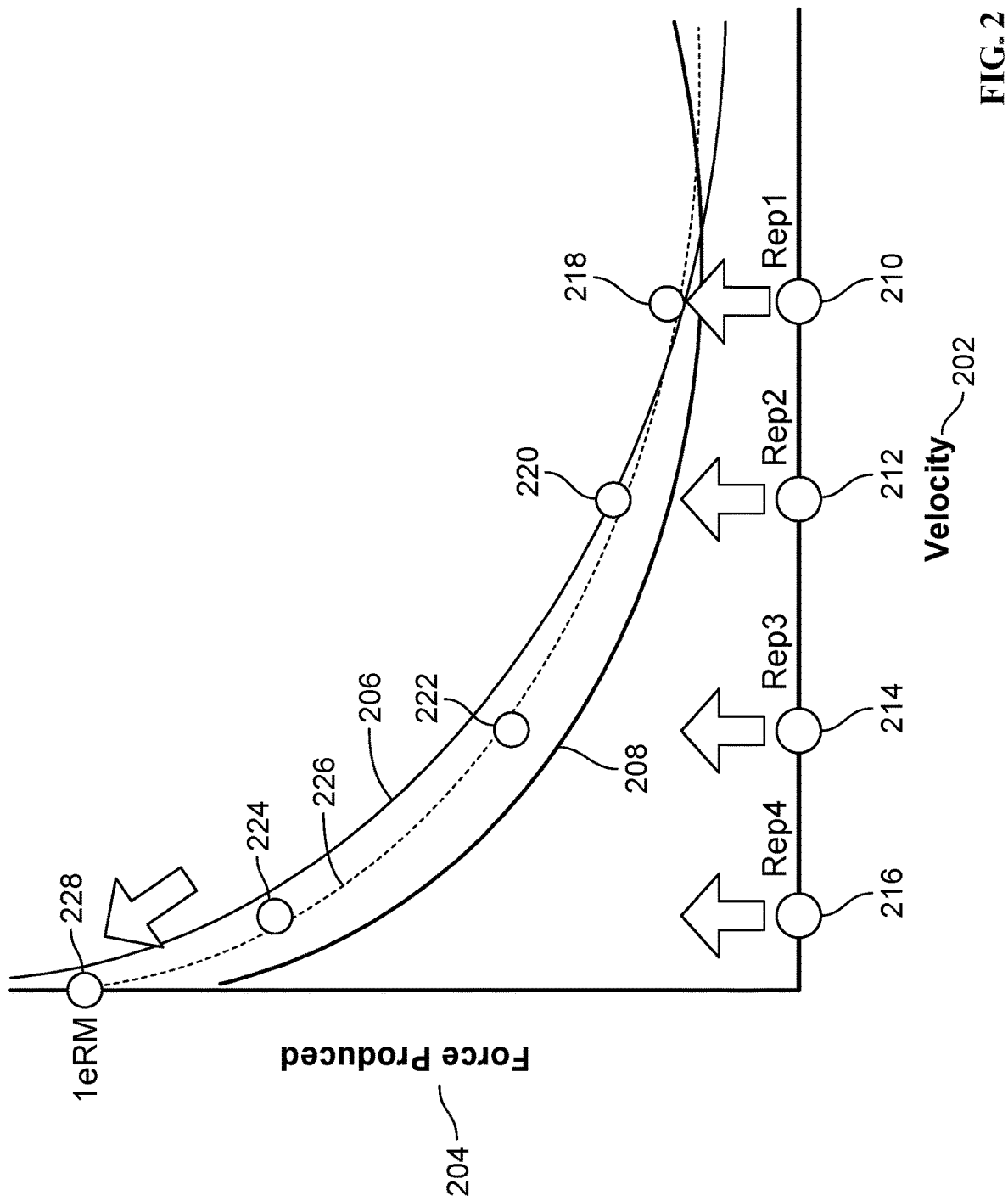
FIG. 2 illustrates an example of strength determination based on isokinetic seed movements.

FIG. 2 illustrates an example of strength determination based on isokinetic seed movements. FIG. 2 is a two-dimensional graph with an x-axis along movement velocity (202) and a y-axis along force produced (204) for that movement. For a given movement, using empirical studies one or more theoretical FVPs (206), (208) may be plotted in general for a typical human being in general, or for a typical human being of a given age, sex, and/or other demographic/physical characteristics.

Using the machine of FIG. 1, the machine prompts and manifests isokinetic seed movements for the user to perform. At least one isokinetic seed movement is needed to determine strength, and practically 3-4 of the same isokinetic seed movement at different speeds may be used to determine strength with greater accuracy. As well, 3-4 different isokinetic seed movements may be used to determine strength for different muscle groups.

From data gathered on these isokinetic seed movements, the maximum weight may be estimated as a 1eRM for the user for movements associated with the isokinetic seed movements performed in a normal, non-isokinetic way, for example smoothly concentric and eccentric. That maximum weight may be used to estimate proper weight for multiple reps, for example 10 reps or 15 reps, of the associated movement in normal/everyday exercise.

In one embodiment, the same data for a few isokinetic seed movements may be used to recommend starting weight for a broad selection of movements that are not necessarily the isokinetic seed movements. In one embodiment, an ongoing recalibration of the strength determination is done without requiring the user to repeat the isokinetic seed movements; instead, the user's performance on each movement is used to update a user's strength level determination.

In the example shown, the machine of FIG. 1 prompts and/or demonstrates to the user how to use the handles and/or attachments (110) to perform an isokinetic seed movement. The machine may manifest three or four isokinetic seed movements for the user to perform. In one embodiment, the machine uses video prompts on a monitor, and for the isokinetic seed movement, the user mimics what they see in the video and are instructed to move the actuator (110) as fast and as powerfully as they possibly can. The machine's resistance dynamically changes to match the user's applied force, while allowing the user to move the resistance at a prescribed constant speed during the concentric phase, establishing for a given speed (210), for example 50 inches/second, a corresponding produced force (218).

The movements are selected to evaluate different muscle groups in the body, and primarily are aimed at lower body, upper body pushing, upper body pulling, and core, and to be easy to perform with proper form and low risk of injury. In one embodiment, the movements used are a seated lat pulldown, a seated overhead press, a bench press, and a neutral grip deadlift. In another embodiment, the movements used exclude bench press or could replace bench press with a movement that focuses on core/abdominal motion.

The machine generates data from these isokinetic seed movements. In one embodiment, at 50 hz, the machine adjusts the force needed to match the user and maintain a constant prescribed speed. In one embodiment, speed is varied between 20-60 inches/second, decreasing each rep. This time series data is stored during the reps in memory and also to log files that may be stored locally and/or in the cloud with an account associated with the user.

In one embodiment, a second rep of the isokinetic seed movement is performed after an appropriate rest, for example at 45 inches/second (212) a second produced force (220) is established. In one embodiment, a third rep of the isokinetic seed movement is performed after an appropriate rest, for example at 35 inches/second (214) a third produced force (222) is established. In one embodiment, a fourth rep of the isokinetic seed movement is performed after an appropriate rest, for example at 30 inches/second (216) a fourth produced force (224) is established.

With one data point (218) or more (220, 222, 224) data points, a FVP (226) may be estimated for the user. This FVP (226) may intercept the y-axis at point (228), which represents the 1eRM of the user.

Thus with at least one isokinetic seed movement, and practically with 3-4 reps of an isokinetic seed movement at varying speeds, by comparing an amount of force resisted at each given velocity, extrapolation may permit a slope to be drawn and an 1eRM determination is made based on the drawn slope. With the 1eRM, with traditional repetition values associated with specific percentages of a 1eRM, recommendations may be made for different weights.

The machine determines user's strength level from at least one and practically with 3-4 isokinetic seed movements on the machine. The force and speed time series data stored during the reps may be used to find the 1eRM the user could perform at each movement. In one embodiment, noise is first removed from sensor measurements. For example, smart average-like values of the speed at which the user acted against the force of resistance are found based at least in part on historical data for a particular machine with its inherent friction/sensor noise and/or for a particular user with their anatomical and physiological past history.

The velocity and force pair determine a one rep maximum that the user can lift, using a traditional relationship/tradeoff between how much force and velocity the human body can generate as shown in FIG. 2, when isokinetic force has been historically observed/studied to determine specific FVP for a movement. The 1eRM is the force at a speed of approximately zero in an FVP. The FVP relationship is based on data collected from many users for each movement, as the relationship varies for each different movement. Using the velocity and force pair the user performed, the 1eRM (228) may be found by following along the FVP (226) to a near-zero velocity. In one embodiment, the user's best result is taken should they try the entire process multiple times.

Once a 1eRM has been calculated, respective rep/weight recommendations may be made based on traditional "rep-percentage" charts which are known in the field to equate a 1eRM to a suggested weight for 10 reps, for example. Practical adaptation includes a suitable attenuation of a recommendation for practical reasons, for example recommending using the rep-percentage charge based on specific rep or percentages may naively recommend a user "do 10 reps at 75% of their 1eRM". This would rate these reps at 9-10 out of 10 on a relative perceived exertion scale and physically the user may not be able to replicate the recommendation across multiple sets. Knowing this, the scale may be attenuated by 10-15% and then those values equated to accommodate physiological fatigue. A final suggestion based on a 1eRM determination may be to "do 10 reps at (60%) of 1eRM", which is still personalized to the user and accounts for fatigue across multiple sets, say 4-6 sets.

In one embodiment, using isokinetic seed movements of seated lat pulldown, a seated overhead press, a bench press, and a neutral grip deadlift, the list of movements with a starting strength determination and rep suggestion may be extrapolated to include those in Table 1 below:

TABLE 1

Extrapolated movements available from seed movement.

| | |
|---|---|
| ½ Kneeling Pallof Press | Resisted Step Up |
| ½ Kneeling Stability Chop | Single Arm, Single Leg RDL |
| ½ Kneeling Stability Lift | Single Leg RDL |
| Bird Dog w/ Row | Split Squat |
| Inline Stability Chop | Sumo Deadlift |
| Inline Stability Lift | ½ Kneeling Alternating Overhead |
| Iso Split Squat Pallof Press | Press |
| Iso Split Squat Stability Chop | ½ Kneeling Chop |
| Iso Split Squat Stability Lift | ½ Kneeling Lift |
| Kneeling Cable Crunch | ½ Kneeling Overhead Press |
| Lateral Bridge w/ Row | ½ Kneeling Single Arm Overhead |
| Pillar Bridge w/ Row | Press |
| Pullover Crunch | ½ Kneeling Single Arm Row |
| Rotational Chop | Alternating Bench Press |
| Rotational Lift | Alternating Neutral Lat Pulldown |
| Single Leg Pallof Press | Barbell Bent Over Row |
| Single Leg Stability Chop | Bench Press |
| Single Leg Stability Lift | Bent Over Row |
| Standing Pallof Press | Chinup |
| Tall Kneeling Pallof Press | Front Raise |
| Barbell Deadlift | Hammer Curl |
| Barbell RDL | Inline Chest Press |
| Bulgarian Split Squat | Inline Chop |
| Front Squat | Inline Lift |
| Goblet Curtsey Lunge | Iso Split Squat Chest Press |
| Goblet Reverse Lunge | Iso Split Squat Chop |
| Goblet Split Squat | Iso Split Squat Lift |

TABLE 1-continued

Extrapolated movements available from seed movement.

| | |
|---|---|
| Goblet Squat | Lateral Raise |
| Neutral Grip Deadlift | Neutral Lat Pulldown |
| Pull Through | Seated Lat Pulldown |
| Resisted Lateral Lunge | Seated Overhead Press |
| Seated Row | Barbell Bench Press |
| Single Arm Bench Press | Barbell Bent Over Row |
| Single Arm Bent Over Row | Barbell Bicep Curl |
| Single Leg Chop | Barbell Chinup |
| Single Leg Standing Chest Press | Barbell Deadlift |
| Single Leg Standing Lift | Barbell Front Raise |
| Standing Barbell Overhead Press | Barbell Front Squat |
| Standing Face Pull | Barbell Lateral Leg Raise |
| Standing Incline Press | Barbell Lying Glute Bridge |
| Standing Overhead Press | Barbell RDL |
| Supinated Curl | Barbell Seated Lat Pulldown |
| Tall Kneeling Single Arm Chest Press | Barbell Seated Overhead Press |
| | Barbell Skull Crusher |
| Tall Kneeling Single Arm Lat Pulldown | Barbell Straight Arm Pulldown |
| | Barbell Sumo Deadlift |
| Tricep Extension | Bar Move |
| Tricep Kickback | Bench Chest Fly |
| Upright Row | Bench Press |
| X-Pulldown | Bent Hollow Rocking |
| X-Pulldown w/ Tricep Extension | Bent Knee Calf Raise |
| Y-Pull | Bent Over Row |
| 90-90 Arm Sweep | Bicep Curl |
| 90-90 Hip Stretch | Bird Dog |
| Alternating Bench Press | Goblet Curtsey Lunge |
| Alternating Bicep Curl | Goblet Reverse Lunge |
| Alternating Neutral Lat Pulldown | Goblet Split Squat |
| Assisted Reverse Lunge | Goblet Squat |
| Assisted Squat | Half Kneeling Alternating Overhead Press |
| Bird Dog w/ Row | |
| Bodyweight Bulgarian Split Squat | Half Kneeling Chop |
| Bodyweight Single Leg RDL | Half Kneeling Lift |
| Bodyweight Split Squat | Half Kneeling Overhead Press |
| Bodyweight Squat | Half Kneeling Pallof Press |
| Bretzel Stretch | Half Kneeling Single Arm Overhead Press |
| Bulgarian Split Squat | |
| Burp | Half Kneeling Single Arm Row |
| Burpee | Hammer Curl |
| Butt Kicker | Hamstring Walkout |
| Cat-Cow | Handle Move |
| Close Grip Barbell Bench Press | High Knee |
| Crunch | Hip Raise |
| Dead Bug | Hollow Body Rocking |
| Decline Chest Fly | Incline Chest Fly |
| Elevated Glute Bridge | Incline Pushup |
| Elevated Single Leg Glute Bridge | Inline Chest Press |
| External Shoulder Rotation | Inline Chop |
| Farmer March | Lying Bicep Curl |
| Floor Slide | Lying Face Curl |
| Foot Elevated Lateral Bridge | Lying Hamstring Stretch |
| Foot Elevated Pushup | Marching Glute Bridge |
| Front Raise | Middle Chest Fly |
| Inline Lift | Mountain Climber |
| Internal Shoulder Rotation | Mountain Climber Twist |
| Iso Split Squat | Neutral Grip Deadlift |
| Iso Split Squat Chop | Neutral Lat Pulldown |
| Iso Split Squat Lift | Neutral Single Arm Straight Arm Pulldown |
| Iso Split Squat Pallof Press | |
| Iso Split Squat Single Arm Chest Press | Overhead Tricep Extension |
| | Pillar Bridge |
| Iso Squat Hold | Pillar Bridge w/ Row |
| Jumping Jack | Plank Jack |
| Jump Lunge | Plank to Toe Tap |
| Jump Squat | Plank w/ Reach |
| Kneeling Cable Crunch | Prone Shoulder Sweep |
| Kneeling Oblique Cable Crunch | Pullover Crunch |
| Lateral Bench Jump | Pull Through |
| Lateral Bridge | Pushup |
| Lateral Bridge w/ Rotation | Reverse Lunge w/ Hop |
| Lateral Bridge w/ Row | Reverse Lunge w/ Single Arm Row |
| Lateral Crawl | Rope Move |
| Lateral Lunge | Rotational Chop |
| Lateral Mountain Climber | Rotational Lift |
| Lateral Raise | Rotational Row |
| Leopard Crawl | Runners Lunge |

TABLE 1-continued

Extrapolated movements available from seed movement.

| | |
|---|---|
| Pushup to Plank | Scapular Pushup |
| Quad Hip Stretch | Seated Alternating Bicep Curl |
| Quad Hip Stretch w/ Bench | Seated Alternating Overhead Press |
| Quadruped Hip Circle | Seated Bicep Curl |
| Racked Reverse Lunge | Seated Lat Pulldown |
| Reach and Rotate Closer | Seated Overhead Press |
| Reach and Rotate Opener | Seated Pallof Press |
| Resisted Calf Raise | Seated Row |
| Resisted Dead Bug | Seated Single Arm Lat Pulldown |
| Resisted Glute Bridge | Seated Single Arm Overhead Press |
| Resisted Hip Raise | Shoulder Shrug |
| Resisted Lateral Lunge | Shoulder Tap Plank |
| Resisted Leg Lowering | Single Arm Bench Press |
| Resisted Leg Raise | Single Arm Bent Over Row |
| Resisted Step Up | Single Arm Deadlift |
| Rest | Single Arm Decline Chest Fly |
| Reverse Fly | Standing Chest Press |
| Reverse Grip Barbell Bicep Curl | Standing Chop |
| Reverse Grip Barbell Tricep Extension | Standing Decline Chest Press |
| | Standing Face Pull |
| Reverse Grip Bicep Curl | Standing Incline Press |
| Reverse Grip Tricep Extension | Standing Lift |
| Reverse Lunge | Standing Overhead Press |
| Single Arm Incline Chest Fly | Standing Pallof Press |
| Single Arm Lateral Leg Swing | Standing Single Arm Row |
| Single Arm Resisted Leg Raise | Step Up |
| Single Arm Single Leg RDL | Straight Arm Pulldown |
| Single Arm Squat w/ Row | Suitcase Deadlift |
| Single Arm Tricep Extension | Suitcase March |
| Single Leg Chop | Suitcase Reverse Lunge |
| Single Leg Dead Bug | Sumo Squat Stretch |
| Single Leg Glute Bridge | Superhero Iso Hold |
| Single Leg Pallof Press | Tall Kneeling Pallof Press |
| Single Leg RDL | Tall Kneeling Single Arm Chest Press |
| Single Leg Standing Chest Press | |
| Single Limb Bird Dog | Tall Kneeling Single Arm Lat Pulldown |
| Skater Bound | |
| Skull Crusher | Tricep Extension |
| Spiderman Crawl | Tricep Kickback |
| Split Squat | Wide Grip Barbell Bench Press |
| Sprinter Crunch | X-Pulldown |
| Squat Jack | X-Pulldown w/ Tricep Extension |
| Squat to Press | Y-Pull |
| Squat w/ Row | |
| Standing Alternating Push-Pull | |
| Standing Barbell Overhead Press | |
| Upright Row | |
| V-Up | |
| Waiter March | |
| W-Hold | |

In one embodiment, a goal of the one or more isokinetic seed movements and/or seed movements from a progressive calibration is to determine a user's FVP for a user's muscle group. As described above, with an FVP there are two estimations and/or determinations that may be made. First, the FVP in part determines a 1eRM. Second, recommended starting weights based on percentage 1eRM charts derived through accepted industry norms are available. Again, to be sure a user does not injure themselves on their first set of 10 reps, for example their 15 rep maximum weight is instead computed and recommended, wherein the 15 rep maximum weight is the weight at which a user may do 15 reps but not 16. This 15 rep maximum weight is determined from percentage 1eRM charts traditionally available.

For example, it is determined that a given user has a 1eRM of 50 lb using the machine in FIG. 1 and the technique described above with isokinetic seed movements. According to a traditional percentage 1eRM chart, a 10 rep max may use a weight equal to 75% of the 1eRM, or 37.5 lb. This may be too heavy as the user may only be able to complete a single set of 10 reps. Instead, an adjustment between 10-15% may be made. For example, if a 10% adjustment is made associated with a 15 rep max, then 75%-10%=65% of the 1eRM, which is 32.5 lb. The 10 rep suggestion then would be equivalent to the 15 rep max, producing the suggestion that a user do 32 lbs for 10 reps to start.

In one embodiment, determining a user's FVP for a user's muscle group is related to solving the isokinetic model:

$$F = B(t)\exp(-a(t)v)$$

wherein F and v are the produced force and movement speed, respectively.

There are at least three sets of information following from a user's FVP:

Strength Calibration—For a given movement and as described herein, given a FVP $a(t_i)$ at the range of motion given at time $t_i$ the value of $B(t_i)$ is solved for, which is the value of F at v=0, or the 1eRM;

Strength Typing—For a given movement, strength typing involves determining an FVP $a(t_i)$ at the range of motion given at time $t_i$ for a plurality of users. The predetermined FVP, or strength typing, may be established using a pool of users who perform the given movement one or more times and using linear regression and/or other statistical modeling techniques, including, for example, a higher order polynomial-based statistical analysis; and Force-Time Prediction—For a given movement, over a range of motion and/or over time t, both the 1eRM, or B, and LVP, or a, may vary. Force-time prediction analysis determines the corresponding variations over time and plots them as a function of index t. This in turn allows a tracking of translation and/or rotation of the actuator (110) to give coaching and correction to the user on form of an entire movement.

By isolating a force-range of motion curve as in force-time prediction, there are expected tension curves produced throughout ranges of motion. In one embodiment, capture technology including motion capture, force platforms, and inverse kinematics analysis enhances such analysis. In one embodiment, isolating these curves, parsing out sections of the range of motion to determine prime movement, and then implementing an adaptive training protocol to align those curves with expected training needed is performed. This also improves injury prediction.

Suggested Weights Logic Examples. In one embodiment, suggested weights logic and/or processing is implemented in controller circuit (104) and/or filter (102) in FIG. 1, and/or in an external device not shown in FIG. 1 and communicated to controller circuit (104) and/or filter (102). The following are examples of determining suggested weights for a user's exercise movement.

Example of Suggesting Lower Weight After Being Spotted. An exercise machine that controls motor torque to affect resistance may provide "spotting" to a user.

Consider, for example, a scenario where a user is in the middle of a concentric phase and reaches a point where they cannot complete the range of motion because they are fatigued. This is a common scenario in weight lifting, and may be considered poor form because the user cannot complete the range of motion. However, if the system of FIG. 1 detects this scenario it may "spot" the user, analogous to a human spotter for weight lifting, for example:

1. A user begins by pulling the actuator (110) of FIG. 1 through the range of motion;
2. The user's range of motion is between pre-determined motion thresholds, for example 5% and 80%;

3. The velocity of the cable (108) of FIG. 1 drops to zero, or below some pre-determined velocity threshold close to zero;
4. Even at a low velocity, measured and/or calculated tension applied by the user is found to be above a pre-determined tension threshold for f, the perceived resistance force, based at least in part on torque exerted by motor (106) of FIG. 1;
5. The tension and low velocity persists for a pre-determined period of time, for example 0.5 seconds; and/or
6. The system responds by slowly reducing f, for example linearly over the course of 2 seconds from 100% of starting/current f to a pre-determined force threshold, for example 90% of starting f or 5 lbs. Alternatively, the force is reduced at a fixed absolute rate, such as 20 lbs/sec, regardless of f. As soon as velocity rises above some pre-determined velocity threshold such as 5 cm per second, m stops reducing, and a new function adjusts m through the remainder of the range of motion. Two examples of a new function is a post-spot function or a scaled version of the prior function that the user got stuck on.

In one embodiment, spotted reps are treated the same way that uncompleted reps, or "failed reps", are treated. For example a user may be in an exercise regime that includes 4 sets of 10 reps of 100 lb of a bench press movement, so each set has a "rep count" of 10 reps. In one embodiment, if a user misses this rep count by n reps, the weight is lowered to adjustWeightForRepGoal(100, 10−n+1, 12), such that the amount that the weight decreases by falls in the range of [1, 15%×base_weight] pounds, where the base_weight is 100 lb in this example. The weight is adjusted from a rep goal of 10+n−1 to a rep goal of 12 because someone who failed the rep goal had at most 1 rep in reserve, and users ideally have 2 reps in reserve at the end of a set. Given that in this example, about 10% is typically taken off, if the weight is deemed too heavy to complete the rep count, 10% of the base_weight may be defined as the minimum threshold of being spotted that is counted as a failed rep. The suggested weight may then be 90% of the base_weight for the next set, or 90 lb.

In one embodiment, if somebody is spotted on the last rep of their set, that may be considered simply a healthy way of the user pushing themselves to the limit/burning out, and so it may not be a desirable user experience to lower the weight in that case. The suggested weight for the next set may remain the last base_weight of 100 lb in this example.

In one embodiment, if somebody is spotted in a set at all, that set is not used as proof that a suggested weight should increase over the last weight/base weight. However, if somebody is spotted in a rep that comes after exceeding the "rep goal", then it may be recognized that that person was able to complete the prescribed reps at the prescribed weight, and the weight progression may be treated like a set that was completed properly. A "rep goal" as referred to herein is any goal set by user, coach, and/or system for a number of reps in a given set for a specified movement.

One example of how suggested weights may be adjusted from one set to the next in a workout in the event a user is spotted is a "Spotted Before Meeting the Rep Count Goal" protocol:

If a user is spotted at least 10% of base weight on a rep before the last rep of the rep count goal, for example, with a rep count goal of 10, spotted 10% of base weight on rep 9 or earlier, then reduce the weight to adjustWeightForRepGoal(100, 10−n+1, 12), where n is the number of missed reps, such that the amount that the weight decreases by falls in the range of [1, 15%×base_weight] pounds;

If a user is spotted at least 10% of the base weight for the first time in the set on the last rep of the rep count goal, for example with a rep count goal of 10, spotted 10% of the base weight on rep 10, spotted less than 10% of base weight on reps 1-9, then do not lower the suggested weight for the next set and/or treat the set similarly to how other sets that are spotted are treated; and/or If a user's maximum spotted weight of a set before meeting 100% of the rep count goal is less than 10% of base weight, then do not lower the suggested weight for the next set and/or treat the set similarly to how other sets that are spotted are treated.

One example of how suggested weights may be adjusted from one set to the next in a workout in the event a user is spotted is a "Spotted After Meeting The Rep Count Goal" protocol:

If a user is spotted after meeting the rep count goal, for example with a rep count goal of 10, spotted for the first time in the set on rep 11 or later, then treat the set similarly to as how a set where the user successfully met the rep count goal without being spotted is treated. For example, with a rep goal of 10, if user is spotted on the 11th rep, treat the set as though they did 10 unspotted reps.

Example of Suggesting Lower Weight After Long Breaks. If a user has been inactive on a strength trainer/exercise machine for a long time—for example at least three weeks, or any other period of time as appropriate—a suggested weight may be a lower weight than the last weight exercised before the long break. In one embodiment, a suggested weight may be a weight that is lowered at a higher rate than at which a suggested weight would be lower otherwise. For example, if during normal workout sessions a suggested weight was 10% lower for a failed seventh rep and 5% lower for a failed eighth rep, after a long break a similar suggested weight may be 20% lower for a failed seventh rep and 15% lower for a failed eighth rep.

Typically a user finds a home digital strength trainer one of the most convenient means of strength training, so if the exercise machine is being unused, it is unlikely that they are instead going to the gym. In one embodiment, the suggested weight for a movement is lowered if a user has not worked the muscle groups associated with that movement in at least the last three weeks or any other time period as appropriate.

In one embodiment, to start the "primary muscle group" and "secondary muscle group" of a movement are focused on, and it is determined whether either one has been worked as either a primary mover or secondary mover in at least the last three weeks. For example if a user is doing a bench press and has not worked on chest muscle groups or arm muscle groups for more than three weeks, a suggested weight may be a drop of 15% from the last bench press. In one embodiment, care is taken to not drop the weight too far, as weight progressions may not ramp the user back up to previous strength quickly enough.

As referred to herein, a "primary muscle group" is one with the highest muscle utilization value (0-100 scale) for a given movement. These are the muscles targeted by the movement and used intensely. One example is for the movement Neutral Grip Deadlift, which has Hamstrings as its primary muscle group. Another example is that of the movement Bench Press, which has a primary muscle group of Chest.

As referred to herein, a "secondary muscle group" has the second highest muscle utilization for a given movement. Secondary muscle groups are intensely used, but usually not the limiting factor in how much weight a user can lift. One example is for the movement Neutral Grip Deadlift, which has Glutes as a secondary muscle group. Another example is that of the movement Bench Press, which has Triceps as a secondary muscle group.

In one embodiment, a muscle group protocol for a user performing a move whose primary muscle group is called X, and secondary muscle group is called Y:

- If muscle X has not been worked as a primary or secondary muscle in at least the last three weeks, and neither has muscle Y, then the suggested weight is a drop of the last exercised weight of that movement by 15%; and/or
- If muscle X or muscle Y has been worked either as a primary muscle or secondary muscle in at least the last 3 weeks, then the suggested weight is the same as the last exercised weight of that movement.

A triceps-based example of determining suggested weights based on muscle groups includes:

- If a user is starting a triceps extension movement, and has done triceps-focused/triceps-primary movements such as triceps kickbacks in the past three weeks, then the suggested weight for the current triceps extension movement may be the same base weight as the last triceps extension movement, even if that took place longer than three weeks ago.
- If a user is starting a triceps extension movement, and has not done any triceps-focused/triceps-primary movements such as triceps kickbacks in a month, but has done bench press movements which are triceps-secondary within the past 3 weeks, then the suggested weight for the current triceps extension movement may be the same base weight as the last triceps extension movement, even if that took place longer than three weeks ago.
- If a user is starting a triceps extension movement, and has not done any triceps-focused/triceps-primary movements such as triceps kickbacks in the past 3 weeks, nor any triceps-secondary movements within the past 3 weeks, then the suggested weight for the current triceps extension movement may be to drop the next weight to max(1, 15%×base_weight) lb.

In one embodiment, key performance indicators ("KPI") are tracked and/or used to contribute to determining suggested weights. For example, detecting a decrease in a KPI representing the number of times/amount by which a user manually lowers the weight for one or more movements after they return to the exercise machine from a long break may itself trigger a suggested weight of a lower amount for all other movements.

In one embodiment, features are used to contribute to determining suggested weights. For example, secondary muscle groups may be tracked more closely and/or tertiary muscle groups may be used. For example, different suggested weight "trajectories" may be used, such as aggressively lowering a suggested weight for first few movements to reacclimate the user with the movement, and then aggressively ramp up suggested weights to where they were before after it is detected they are reacclimatized. For example, different suggested weight reductions may be used for different movement families, rather than using a static weight reduction such as 10% or 15%.

Example of Increasing Suggested Weight After Rep Goal is Exceeded. If a user has exceeded their rep goal by a large amount, they are far more likely to increase the weight on the next set than they otherwise would. In one embodiment, when a user exceeds the rep goal, instead of just increasing the weight by one to two pounds, the weight is adjusted for the rep count they just completed. For example, if they completed 15 reps at 50 pounds when the rep count goal was 10, the next set's suggested weight is set as the "10-rep equivalent" of doing 50 pounds for 15 reps.

Figure 3A:
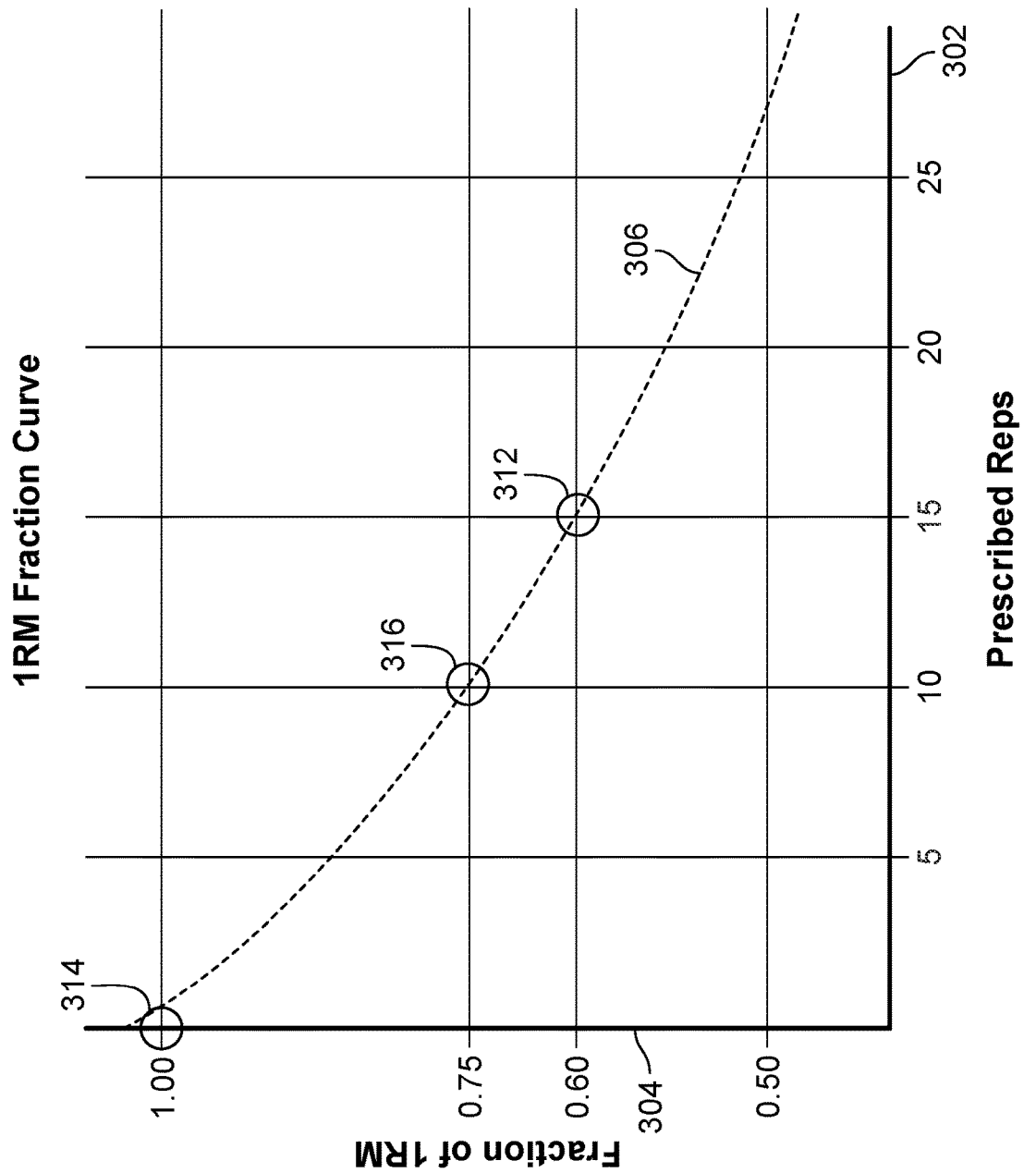
FIG. 3A illustrates an example of rep equivalent determination based on an 1RM fraction curve.

FIG. 3A illustrates an example of rep equivalent determination based on an 1RM fraction curve. FIG. 3A is a two-dimensional graph with an x-axis along prescribed reps (302) and a y-axis along a fraction of one-rep maximum (1RM) (304) for a given movement. For a given movement, using empirical studies one or more curves (306) may be plotted in general for a typical human being in general, or for a typical human being of a given age, sex, and/or other demographic/physical characteristics.

As referred to herein, an "X-rep equivalent" is determined at least in part by finding the 1RM of 50 pounds for 15 reps from data point (312) on the curve, which shows that 15 reps of 50 lb are equivalent to an 1RM of 50 lb÷60%=83.3 lb (314). Converting the 1RM of 83.3 lb to a 10-rep equivalent weight may be made in part by following the curve to point (316), or 83.3 lb×75%=62.5 lb, a suggested weight increase of 12.5 lb. In one embodiment, the set-by-set weight increases are limited to a maximum, for example 10 pounds, to reduce user safety issues with high spikes of increased weight.

In one embodiment, when an empirical curve is unavailable an analytical curve is used, for example one formula for suggesting weight after a rep count goal is exceeded is:

$$suggestedWeight = previousWeight \times \frac{getFrac1(repCountGoal)}{getFrac1RM(repCount)}$$

where suggested Weight is the suggested weight for a movement, previous Weight is the previous weight lifted for the movement, repCount is the previous exceeded rep count for the movement, and repCountGoal is the upcoming rep count goal for the movement, and $$getFrac1RM(x) = 70\% \times e^{-K(x-1)} + 30\%$$

$$K = -0.048609$$

under the constraint $$1 \leq suggested\ Weight - previousWeight \leq 10$$

This determination for suggested Weight, referred to herein as an "adjustWeightForRepCountGoal" determination, may also be used to scale weights to sets with different rep count goals, and/or to increase/decrease weights.

Two-sided movements—those that have a "left side" and "right side" such as bicep curls—are limited by the weaker side. In one embodiment, if the rep count goal is 10 and the user did 12 reps on one side and 15 on the other, the set is treated as though they did the lower number, 12 reps, on both sides. In one embodiment, if the user exceeds the rep goal on one side but does not exceed the rep goal on another side, the set is treated as though they did not exceed the rep goal.

In one embodiment, key performance indicators ("KPI") are tracked and/or used to contribute to determining suggested weights. For example, detecting a decrease in a KPI representing the number of times/amount by which people manually increase the weight after they exceed the rep goal by a large amount for a given movement may trigger a suggested weight of a greater amount for all other movements.

Suggesting Starting Weights. Users may perform strength determination/calibration as described above to suggest a starting weight. In one embodiment, users perform one set of four moves with three reps in the baseline and/or isokinetic mode to determine a suggested starting weight. In one embodiment, if a user does not do the baseline, a default of a minimal weight is used for a user to improve safety, for example a minimal weight of five pounds.

In one embodiment, an improved feature for determining suggested weights based on related movements is used. The improvement is to use additional information from related movements to suggest a starting weight to improve user safety and efficiency of weight training for a user. As described herein, movements with "similar muscle utilization" are movements that have cosine similarity of 0.8 and above when comparing muscle utilization vectors.

Every movement has a corresponding muscle utilization vector, which is a vector composed of each muscle's utilization (0-100 value) as an element, [<calf muscle utilization>, <quadricep muscle utilization>, <hamstring muscle utilization>, <glute muscle utilization>, <back muscle utilization>, <abdominal muscle utilization>, <obliques muscle utilization>, <chest muscle utilization>, <shoulder muscle utilization>, <bicep muscle utilization>, <tricep muscle utilization>, <forearm muscle utilization>]. Cosine similarity is a mathematical function that takes as input two vectors of any and/or equal length, and returns the cosine of the angle between them. For example, the Bench Press movement may have a muscle utilization vector of [0, 0, 0, 0, 0, 3, 1, 95, 25, 0, 30, 0] and the Pushup may have a muscle utilization vector of [0, 0, 0, 0, 0, 5, 0, 60, 10, 0, 25, 0]. Notice the largest muscle utilization in each vector belongs to the chest muscle. The cosine similarity of these two vectors is 0.991.

In the event this feature is used:
if the user has done a threshold number of movements (for example, four movements) with similar muscle utilization, then the 1RM of this current movement is considered to be 90%×median of the best normalized 1RM of each movement with similar muscle utilization and a suggested starting weight for a given prescribed rep set is based on the 1RM of the current movement using a curve and process similar to that described above in associated with FIG. 3A. 1RMs for each movement are "normalized", as referred to herein, using population distributions of weights used for each move, for example, using the percentile within each movement's weight distribution;
else the starting suggested weights for the movement is based on an estimate from the baseline set of moves as described herein for strength determination/calibration.

Suggested Weights for Rep-Based Sets. Rep-based sets as described herein are traditional strength training sets where a user performs a number of sets of a number of prescribed reps. An example might be to do four sets of 10 reps of bench press.

Related Movements. In one embodiment, the improved feature for determining suggested weights based on related movements is used. The improvement is to use additional information from related movements to suggest a weight for a rep-based set to improve user safety and efficiency of weight training for a user. In the event this feature is used:
if a current movement has not been performed before and the user has done a threshold number of sets of movements (for example, four sets) with similar muscle utilization, then the 1RM of this current movement is considered to be 90%×median of the normalized 1RMs of each set of a movement with similar muscle utilization, where the 1RM is normalized in the manner described above, and a suggested starting weight for a given prescribed rep set is based on the 1RM of the current movement using a curve and process similar to that described above in associated with FIG. 3A;
else if the current movement has not been performed in a threshold number of months (for example, four months) preceding a second threshold number of most recent sets of movements with similar muscle utilization (for example, four most recent sets), then the 1RM of this current movement is considered to be 90%× median of the normalized 1RM of each set of a movement with similar muscle utilization, where the 1RM is normalized in the manner described above, and a suggested starting weight for a given prescribed rep set is based on the 1RM of the current movement using a curve and process similar to that described above in associated with FIG. 3A;
else if the current movement has been performed within a last threshold number of months (for example, the last five months), then the suggested weight for the rep-based set is at most a threshold percentage (for example, 10%) of what the current movement was last performed at. For example, if the current movement was last performed at 100 lb, the current movement may now be performed at a suggested weight at 90 lb.

Dynamic Weight Modeling. In one embodiment, the improved feature for determining suggested weights based on dynamic weight modeling is used. Dynamic weight modeling as described herein includes any weight modeling that may change over the movement, for example eccentric weight models that increase weight for a user during the eccentric phase of exercise, chains weight models that model lifting a chain off the ground, with variable resistance during the range of the movement as more of the chain is lifted off the ground, and/or a "smart flex" weight model that matches a user's strength at every point in the range of motion in the movement, as described in U.S. patent application Ser. No. 17/323,277 entitled DYNAMIC STRENGTH LOADING PER MOVEMENT filed May 18, 2021 which is incorporated herein by reference for all purposes.

The improvement is to use previous information from dynamic weight modeling performance to suggest a weight for a rep-based set to improve user safety and efficiency of weight training for a user. In the event this feature is used, the suggested weight including dynamic weight models when checking to see if a user has completed consecutive sets without weight increase and/or what weight to suggest for the next set may use an example formula:

$$suggestedWeight = baseWeight + 25\% \; eccWeight \frac{repGoal - 1}{repGoal} + 35\% \; (smartFlexWeight + chainsWeight) \frac{repGoal - 2}{repGoal}$$

where suggestedWeight is the suggested weight, baseWeight is the current weight for a movement, eccWeight is the additional eccentric phase weight for the movement, smartFlexWeight is the additional maximum smart flex weight for the movement, chains Weight is the additional maximum chains weight for the movement, and repGoal is the rep goal for the movement.

For example, if a first set for a given movement uses a dynamic weight model at 10 lb resistance plus 40% eccentric weight with a rep goal of 10, and the second set has no dynamic weight modeling with the same rep goal, using the above formula the second set suggested weight is 10 lb+25%×4 lb×0.9=10.9 lb which may be rounded to 11 lb.

Weight Percentage. As referred to herein, 'weight percentage' is a fraction of the weight a user is believed to be capable of a given movement and/or set with the given movement. One relationship that may be used is:

$$weightPercentage = \frac{reduced\_baseWeight}{normalWeight} \text{ in } \%$$

where weightPercentage is the weight percentage, the reduced BaseWeight is the resistance used in a current set of a current movement, and normalWeight is the user's normal suggested weight for the current movement. Both of these weights already contain all of the other adjustments, including adjustments for the rep goal.

Using weight percentage to determine suggested weights is disclosed. In one embodiment, the weight percentage of an upcoming set is used to determine which recent sets are looked at to determine a suggested weight. The weight percentage may be used as an indication of workout intensity for a set. For example, 100% weight percentage is indicative of a challenging set. This may be a default for most sets. In some cases, the weight percentage may be lower for less challenging sets. The weight percentage may also be over 100% for an extremely challenging set, even if there is a high likelihood that the user will be unable to complete the set. The weight percentage may be used as an adjustment factor to adjust the intensity or the level of challenge for a set.

In one embodiment, sets where the weight percentage is below a threshold, for example 85%, do not impact a suggested weight for a future set. For example, this may indicate a warmup set, for example at a weight percentage of 60%, which is not indicative of a user's performance and/or ability—put another way, very easy sets are not necessarily a reliable predictor of very heavy sets.

In one embodiment, if an upcoming set's weight percentage is more than a specific threshold, for example 85%, only other sets which were done at a weight percentage over a particular threshold, for example 85%, are used to determine a suggested weight. In one embodiment, if an upcoming set's weight percentage is less than a given threshold, for example 85%, all sets regardless of weight percentage are used to determine a suggested weight.

Increases in Suggested Weights. In one embodiment, suggested weight for a current set of a movement is increased by a determined threshold step in the event that there is a subset of consecutive sets where the user met their rep goal over a superset of sets of the movement. In one embodiment, increases in suggested weight do not occur for user-safety sensitive movements. For example, one technique is:

If the user meets their rep goals for two consecutive sets of a movement or the user meets their rep goals for five consecutive sets in the event they have completed 40 sets for the movement;

And all of the following conditions are met:
1RM in the previous set for the movement is less than or equal to 1RM in the set before the previous set for the movement;
the user did not decrease the weight for this movement within this workout;
a spotter and/or spotter mechanism did not reduce the weight in the previous consecutive sets. Reps that were spotted after the rep count goal may be ignored;
there are more than two reps in reserve ("RIR") at the end of the set; and
the movement is not an Internal Shoulder Rotation or an External Shoulder Rotation, or any other movement indicated as user-safety sensitive;
Then the suggested weight for the movement is increased by whichever is larger: an increase of one pound or an increase of 2.5% over the current base weight.

As referred to herein, RIR is an estimate of how many reps a user may have in reserve before reaching their limit/capacity. Thus if a particular user can only do ten theoretical reps, and they are currently on their eighth rep, their RIR is two.

In one embodiment, a technique for increasing suggested weight is based on exceeding the rep goal. For example, one technique is:

If a user has exceeded their rep goal on a previous set of a movement and a spotter and/or spotter mechanism did not reduce weight in the previous set of the movement;
Then the suggested weight is increased from the previous set of the movement by a minimum of 1 lb and maximum of 10 lb, as a function of previous set weight, previous set reps completed, and upcoming set rep goal, as described above using the adjustWeightForRepCountGoal determination.

Decreases in Suggested Weights. In one embodiment, a suggested weight for a current set for a movement may be decreased based at least in part on a rep goal not being met. For example, one technique is:

If at least one of the following conditions is true:
a user did not meet their rep goal in a previous set of a movement;
a spotter and/or spotter mechanism reduced a user's weight by at least 10% on a rep except the last rep of the set's rep count goal for the movement; or
Then the suggested weight is a weight decreased from the previous set in the same workout by whichever is larger: a decrease of 15% of the current base weight, or a function of weight, reps, and rep goal, for example a function adjust WeightForRepGoal(weight, reps+1, repGoal+2).

But, if a user was spotted or failed the rep goal on the last set of the movement in a workout then the weight for the beginning of the next workout is not reduced.

In one embodiment, if a user has not worked out either the primary or secondary muscle groups associated with a movement in the past time threshold, for example 3 weeks, then the suggested weight is a weight decreased from the previous set in the movement by whichever is larger: a decrease of one pound from the current base weight, or a decrease of 15% of the current base weight.

In one embodiment, if in a user's previous set of a movement in a workout, the user manually increased the weight on their own but failed the rep goal, the next time the user does that movement, they are given the previous set's suggested weight. In one embodiment, they are given a previous set's base weight. In one embodiment, they are given a previous set's base weight adjusted for rep goal. The weight may be adjusted for rep goal computationally using $$suggestedWeight = previousWeight \times \frac{getFrac1(repCountGoal)}{getFrac1RM(repCount)}$$

In one embodiment, a user safety analysis is made and determining a suggested weight comprises decreasing weight to provide user safety.

Two Sided Movements. Two sided movements that have a left-side and right-side, may have specific techniques to accommodate their nature. For example, one technique is:
If either side was below the rep goal, then decrease suggested weight from previous set by the greater of a pound or 10% of the base weight for the movement;
If the following four conditions are met:
the user exceeded their rep goal on both sides;
the user did not reduce the weight for this movement in this workout; and
a spotter and/or spotter mechanism did not reduce the weight by at least 10% on a rep, excepting the last rep, of the set's rep count goal for either side; and
there are more than two reps in reserve ("RIR") at the end of each side;
Then increase suggested weight from previous set for the movement by the greater of a pound or 2.5% of the base weight for the movement;
Else suggest the previous set's weight, for example a second side's weight, optionally adjusted for rep goal.

Suggested Weights for Duration-Based Sets. Duration-based sets as described herein are sets where a user is encouraged to perform as many reps as possible within a given duration. One example of a duration-based set is a traditional high-intensity interval training (HITT) workout. An example might be to do four sets of 30 seconds of bench press. Using a duration-based rep goal equivalent to determine suggested weights for a duration-based set is disclosed.

In one embodiment, for a linear workout, wherein a 'linear workout' is a workout where the coach is doing the workout along with the user at the same pace and is speaking in the video, rather than audio disconnected from the video as with a voiceover for duration-based sets, the first set of a movement uses the suggested weights from previous guided personal training, custom, and/or freelift workouts.

In one embodiment, HIIT workouts have weight percentage reduced to a threshold, for example 90%, as the weight percentage is an indication of workout intensity for a set. The system may stop providing high volume suggested weight decreases, or any suggested weight decreases.

In one embodiment, if the workout with duration-based sets is of the HIIT type, the suggested weight is calculated assuming a rep goal based at least in part on dividing the prescribed duration by a threshold, for example, a rep goal of prescribedDuration/2. Thus for a 30 second set, an assumption is made that the user will do 15 reps in 30 seconds.

In one embodiment, if the workout with duration-based sets is purely strength training, the suggested weight is calculated assuming a rep goal based at least in part on dividing the prescribed duration by a different threshold, for example a rep goal of prescribedDuration/3.5. Thus, for a 30 second set, a rep goal for the user is computed as ~9 reps in 30 seconds.

Suggested weight increases for duration-based sets may happen if a user exceeds the rep goal. For example, for MT type workouts, if a user exceeds their rep goal, the suggested weight for the next set may be set to adjust WeightForRepGoal(weight, repGoal, repCount). For example, for strength training type duration-based workouts, if a user exceeds the rep goal by a threshold percentage, for example 30%, the suggested weight for the next set may be set to adjust WeightForRepGoal(weight, 130%×repGoal, repCount).

Suggested weights for High Volume workouts. High volume workouts as described herein are workouts with total relative muscle volume above a certain threshold for each muscle group. In these high volume workouts, moves with the exceeded muscle group as the primary muscle will have weight percentage reduced linearly depending on the exceeded amount up to 90%. This weight percentage is applied at the beginning of the workout. This feature is devised to preemptively reduce weights for long workouts so users are able to complete the workout without failing midway. If there are multiple muscle groups that are high volume, and a move consists of more than one primary muscle that is high volume, the minimum weight percentage is taken. Relative muscle volume of a set is determined by:

$$\text{relative muscle volume} = num.reps \times \frac{weight}{1RM} \times \text{muscle utilization} =$$
$$num.reps \times 1RM\_fraction \times \text{muscle utilization}$$

Figure 3B:
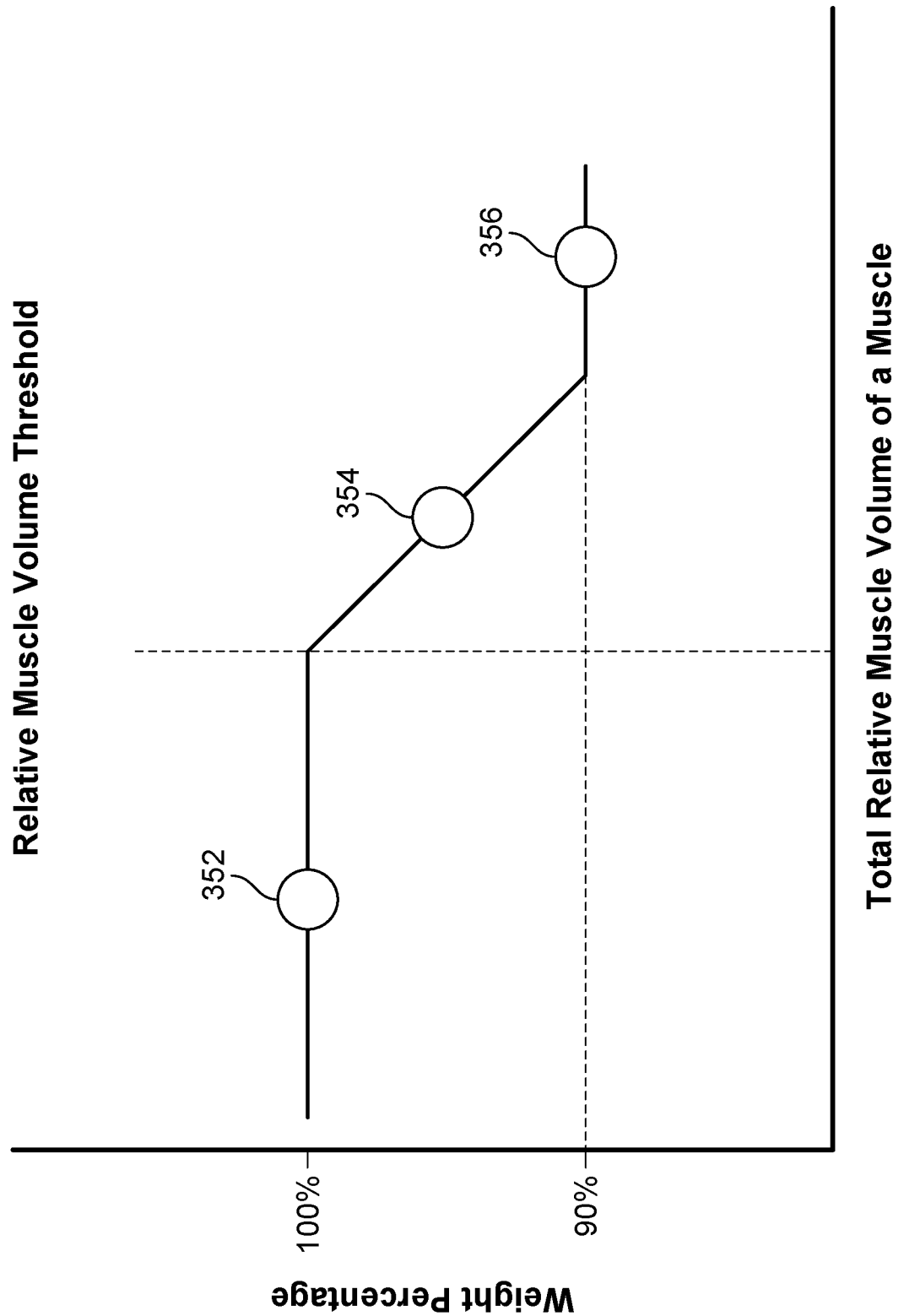
FIG. 3B illustrates one embodiment of linear weight percentage reduction for a particular muscle in a workout.

FIG. 3B illustrates one embodiment of linear weight percentage reduction for a particular muscle in a workout. There is no weight percentage reduction if the total relative muscle volume for a muscle is below the threshold (352). If the threshold is exceeded, reduction is applied linearly (354). When the minimum weight percentage is reached, for example 90%, weight percentage is not reduced further (356).

Figure 4:
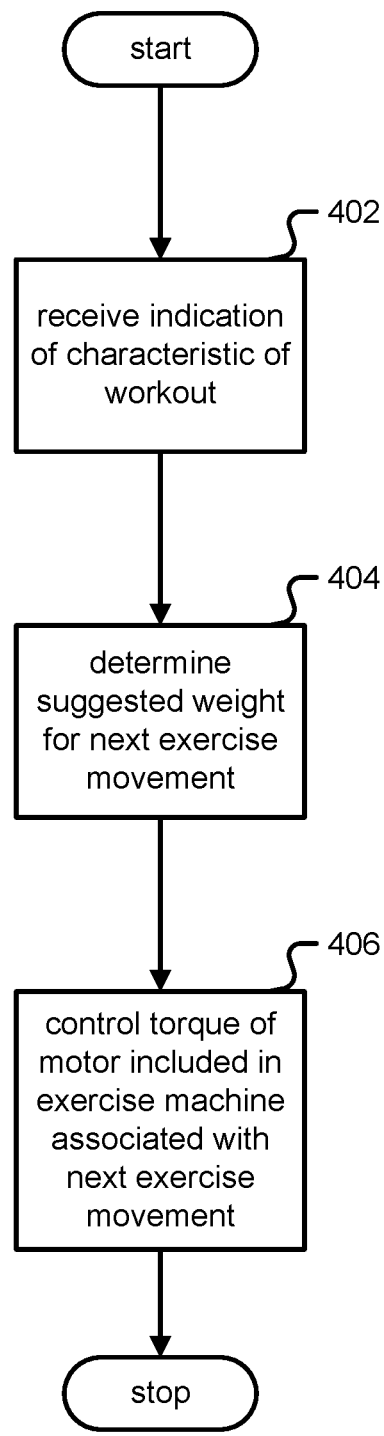
FIG. 4 a flow diagram illustrating an embodiment of a process for determining suggested weights.

FIG. 4 is a flow diagram illustrating an embodiment of a process for determining suggested weights. In one embodiment, controller circuit (104) and/or filter (102) in FIG. 1 carries out the process of FIG. 4. In one embodiment, an external device not shown in FIG. 1 carries out the process of FIG. 4 and communicates to controller circuit (104) and/or filter (102) of FIG. 1.

In step (402), an indication of a characteristic of a workout is received, wherein the workout comprises a next exercise movement.

In step (404), a suggested weight is determined for the next exercise movement, based at least in part on a physiological analysis of the workout characteristic. In one embodiment, the physiological analysis comprises a safety analysis, and determining the suggested weight comprises decreasing weight to provide safety.

In step (406), torque of a motor included in an exercise machine associated with the next exercise movement is controlled, based at least in part on the suggested weight. In one embodiment, the motor of step (406) is the motor (106) of FIG. 1, controlled by motor controller (104).

Figure 5:
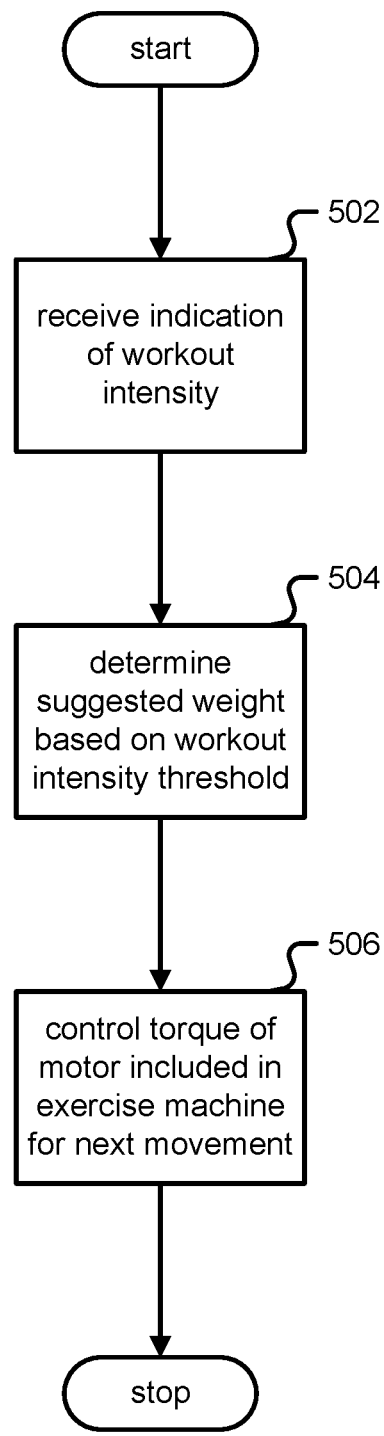
FIG. 5 a flow diagram illustrating an embodiment of a process for determining suggested weights based on workout intensity.

FIG. 5 is a flow diagram illustrating an embodiment of a process for determining suggested weights based on workout intensity. In one embodiment, controller circuit (104) and/or filter (102) in FIG. 1 carries out the process of FIG. 5. In one embodiment, an external device not shown in FIG. 1 carries out the process of FIG. 5 and communicates to controller circuit (104) and/or filter (102) of FIG. 1. In one embodiment, the process of FIG. 5 is an instance of the general process of FIG. 4.

In step (502), an indication of a characteristic of a workout is received, wherein the workout comprises a next exercise movement. In step (504), a suggested weight is determined for the next exercise movement, based at least in part on a physiological analysis of the workout characteristic. In step (506), torque of a motor included in an exercise machine associated with the next exercise movement is controlled, based at least in part on the suggested weight.

In one embodiment, the workout characteristic is workout intensity and the physiological analysis comprises evaluating the indication of workout intensity associated with a previous exercise movement against a threshold. In one embodiment, the indication of workout intensity comprises a weight percentage.

In one embodiment, indication of workout intensity comprises a flag indicating that a past exercise movement comprises a spotted exercise movement, wherein the past exercise movement is not the previous exercise movement. In one embodiment, determining the suggested weight for the next exercise movement comprises reducing a weight of the past exercise movement by a percentage between 5% and 25% in the event the spotted exercise movement is spotted before a rep count goal.

In one embodiment, indication of workout intensity comprises a flag indicating that the previous exercise movement last took place longer than a threshold number of days. In one embodiment, determining the suggested weight for the next exercise movement comprises reducing a weight of the previous exercise movement by a percentage between 5% and 25%.

In one embodiment, indication of workout intensity comprises a flag indicating that a rep count goal of the previous exercise movement was exceeded by more than a threshold. In one embodiment, determining the suggested weight for the next exercise movement comprises increasing a weight of the previous exercise movement by a function of an associated one rep max.

Figure 6:
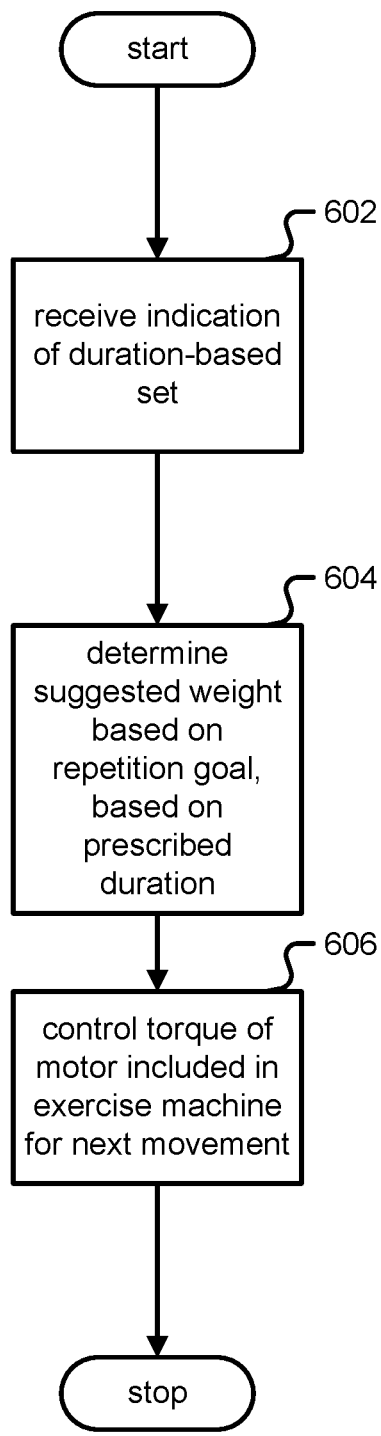
FIG. 6 is a flow diagram illustrating an embodiment of a process for determining suggested weights for duration-based workouts.

FIG. 6 is a flow diagram illustrating an embodiment of a process for determining suggested weights for duration-based workouts. In one embodiment, controller circuit (104) and/or filter (102) in FIG. 1 carries out the process of FIG. 6. In one embodiment, an external device not shown in FIG. 1 carries out the process of FIG. 6 and communicates to controller circuit (104) and/or filter (102) of FIG. 1. In one embodiment, the process of FIG. 6 is an instance of the general process of FIG. 4.

In step (602), an indication of a characteristic of a workout is received, wherein the workout comprises a next exercise movement. In step (604), a suggested weight is determined for the next exercise movement, based at least in part on a physiological analysis of the workout characteristic. In step (606), torque of a motor included in an exercise machine associated with the next exercise movement is controlled, based at least in part on the suggested weight.

In one embodiment, the characteristic comprises a flag indicating that the next exercise movement is part of a duration-based set and the physiological analysis comprises determining a repetition goal based at least in part on a prescribed duration of the duration-based set.

In one embodiment, determining the repetition goal comprises evaluating whether the next exercise movement is a high-intensity training type. In one embodiment, determining the suggested weight for the next exercise movement comprises increasing a weight of the previous exercise movement in the event the repetition goal is met.

Figure 7:
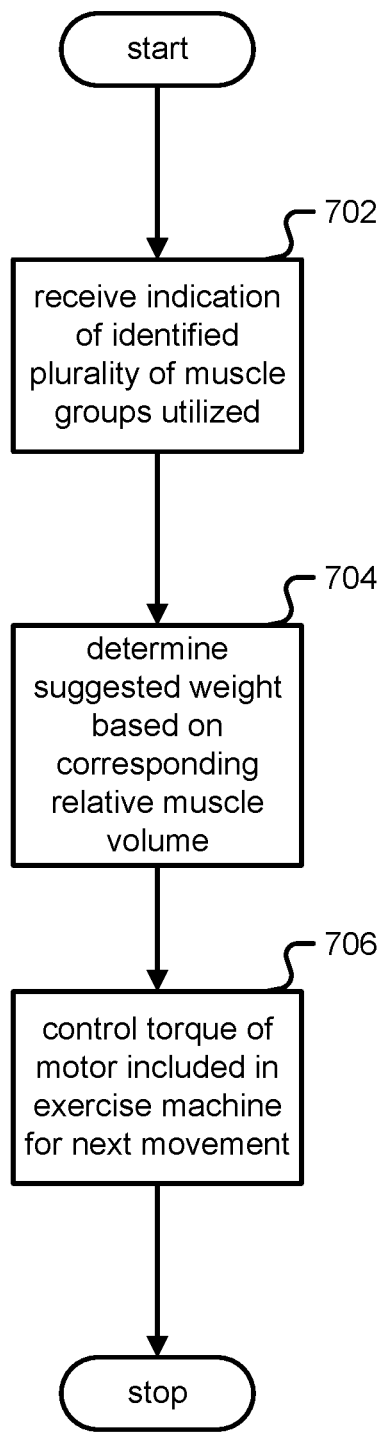
FIG. 7 is a flow diagram illustrating an embodiment of a process for determining suggested weights based on muscle groups.

FIG. 7 is a flow diagram illustrating an embodiment of a process for determining suggested weights based on muscle groups. In one embodiment, controller circuit (104) and/or filter (102) in FIG. 1 carries out the process of FIG. 7. In one embodiment, an external device not shown in FIG. 1 carries out the process of FIG. 7 and communicates to controller circuit (104) and/or filter (102) of FIG. 1. In one embodiment, the process of FIG. 7 is an instance of the general process of FIG. 4.

In step (702), an indication of a characteristic of a workout is received, wherein the workout comprises a next exercise movement. In step (704), a suggested weight is determined for the next exercise movement, based at least in part on a physiological analysis of the workout characteristic. In step (706), torque of a motor included in an exercise machine associated with the next exercise movement is controlled, based at least in part on the suggested weight.

In one embodiment, the characteristic comprises identifying a plurality of muscle groups utilized in the workout, and the physiological analysis comprises determining a corresponding relative muscle volume for each muscle group in the plurality of muscle groups.

In one embodiment, determining the corresponding relative muscle volume comprises determining a function of weight and reps. In one embodiment, the indication comprises a flag indicating that the previous exercise movement in an associated muscle group last took place longer than a threshold number of days, wherein the associated muscle group comprises at least one of the following: a primary muscle group of the next exercise movement and a secondary muscle group of the next exercise movement.

In one embodiment, determining the corresponding relative muscle volume comprises determining a muscle volume for each side of a two-sided movement. In one embodiment, determining the suggested weight is based at least in part on a weaker side of a two-sided movement.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method, comprising:
   receiving an indication of a characteristic of a workout, wherein the workout comprises a next exercise movement, wherein the characteristic comprises a flag indicating that a next exercise movement is part of a duration-based set;
   determining a suggested weight for the next exercise movement, based at least in part on a physiological analysis of the workout characteristic, wherein the physiological analysis comprises determining a repetition goal based at least in part on a prescribed duration of the duration-based set; and
   controlling torque of a motor included in an exercise machine associated with the next exercise movement, based at least in part on the suggested weight.

2. The method of claim 1, wherein:
   determining the repetition goal comprises evaluating whether the next exercise movement is a high-intensity training type.

3. The method of claim 1, wherein determining the suggested weight for the next exercise movement comprises increasing a weight of a previous exercise movement when the repetition goal is met.

4. The method of claim 1, wherein the indication comprises a weight percentage.

5. The method of claim 1, wherein the indication comprises a flag indicating that a past exercise movement comprises a spotted exercise movement, wherein the past exercise movement is not a previous exercise movement.

6. The method of claim 5, wherein determining the suggested weight for the next exercise movement comprises reducing a weight of the past exercise movement by a percentage between 5% and 15% when the spotted exercise movement is spotted before a rep count goal.

7. The method of claim 1, wherein the indication comprises a flag indicating that a previous exercise movement last took place longer than a threshold number of days.

8. The method of claim 7, wherein determining the suggested weight for the next exercise movement comprises reducing a weight of a previous exercise movement by using weights of similar exercise movement of at most 10%.

9. The method of claim 1, wherein the indication comprises a flag indicating that a rep count goal of the previous exercise movement was exceeded by more than a threshold.

10. The method of claim 9, wherein determining the suggested weight for the next exercise movement comprises increasing a weight of the previous exercise movement by a function of an associated one rep max.

11. The method of claim 1, wherein:
the characteristic further comprises workout intensity; and
the physiological analysis further comprises evaluating the indication of workout intensity associated with a previous exercise movement against a threshold.

12. The method of claim 1, wherein determining the repetition goal comprises evaluating whether the next exercise movement is a high-intensity training type.

13. The method of claim 1, wherein determining the suggested weight for the next exercise movement comprises increasing a weight of a previous exercise movement when the repetition goal is met.

14. The method of claim 1, wherein:
the characteristic comprises identifying a plurality of muscle groups utilized in the workout; and
the physiological analysis comprises determining a corresponding relative muscle volume for each muscle group in the plurality of muscle groups.

15. The method of claim 14, wherein determining the corresponding relative muscle volume comprises determining a function of weight and reps.

16. The method of claim 14, wherein the indication comprises a flag indicating that a previous exercise movement in an associated muscle group last took place longer than a threshold number of days, wherein the associated muscle group comprises at least one of the following: a primary muscle group of the next exercise movement and a secondary muscle group of the next exercise movement.

17. The method of claim 14, wherein determining the corresponding relative muscle volume comprises determining a muscle volume for each side of a two-sided movement.

18. The method of claim 17, wherein determining the suggested weight is based at least in part on a weaker side of a two-sided movement.

19. The method of claim 1, wherein the physiological analysis comprises a safety analysis, and determining the suggested weight comprises decreasing weight to provide safety.

20. An exercise machine, comprising:
an actuator;
a motor coupled to the actuator; and
a motor controller coupled to the motor, wherein the motor controller is configured to:
receive an indication of a characteristic of a workout on the actuator, wherein the workout comprises a next exercise movement, wherein the characteristic comprises a flag indicating that a next exercise movement is part of a duration-based set;
determine a suggested weight for the next exercise movement, based at least in part on a physiological analysis of the workout characteristic, wherein the physiological analysis comprises determining a repetition goal based at least in part on a prescribed duration of the duration-based set; and
control torque of the motor for the next exercise movement, based at least in part on the suggested weight.

21. A computer program product, the computer program product being embodied in a non-transitory computer readable storage medium and comprising computer instructions for:
receiving an indication of a characteristic of a workout, wherein the workout comprises a next exercise movement, wherein the characteristic comprises a flag indicating that a next exercise movement is part of a duration-based set;
determining a suggested weight for the next exercise movement, based at least in part on a physiological analysis of the workout characteristic, wherein the physiological analysis comprises determining a repetition goal based at least in part on a prescribed duration of the duration-based set; and
controlling torque of a motor included in an exercise machine associated with the next exercise movement, based at least in part on the suggested weight.

* * * * *